(12) United States Patent
Wu et al.

(10) Patent No.: US 7,514,040 B2
(45) Date of Patent: Apr. 7, 2009

(54) INTELLIGENT BIOSENSING METER

(75) Inventors: Shu-Mei Wu, Taipei (TW); Chia-Chi Wu, Kaohsiung (TW); Chun-Hui Pi, Yonghe (TW); Chao-Wang Chen, Taipei (TW)

(73) Assignee: Taidoc Technology Corporation, Taipei (TW)

( * ) Notice: Subject to any disclaimer, the term of this patent is extended or adjusted under 35 U.S.C. 154(b) by 714 days.

(21) Appl. No.: 11/056,089

(22) Filed: Feb. 14, 2005

(65) Prior Publication Data

US 2006/0182658 A1 Aug. 17, 2006

(51) Int. Cl.
*G01N 33/48* (2006.01)
*G01N 27/28* (2006.01)
*G01N 33/487* (2006.01)

(52) U.S. Cl. .................. 422/68.1; 324/450; 204/403.02

(58) Field of Classification Search ........................ None
See application file for complete search history.

(56) References Cited

U.S. PATENT DOCUMENTS 5,873,990 A * 2/1999 Wojciechowski et al. ... 204/406
2001/0045355 A1 * 11/2001 Gephart et al. .............. 204/400
2002/0002326 A1 * 1/2002 Causey et al. ............... 600/300

* cited by examiner

*Primary Examiner*—Yelena G. Gakh
*Assistant Examiner*—Timothy G Kingan (57) ABSTRACT

An intelligent biosensing meter has a parameter storing unit stored a plurality of parameters that sample strips detection needed and at least one slot for receiving a sample strip or a code card. The code card can store a plurality of parameters therein that are not stored in the parameter storing unit. Therefore, the intelligent biosensing meter not only stores parameters therein but also receives the code card to store new parameter or download new parameter from an internet. Manufacturers can save budget for manufacturing code cards if parameters stored in the biosensing meter are suitable for testing a new batch of sample strip or download from the internet. Furthermore, the intelligent biosensing meter can insert different kind of cards or strips into one slot and recognize them by circuit design to control different functions. The biosensing meter of the present invention will decrease manufacturing cost and be operated easily.

19 Claims, 6 Drawing Sheets

FIG.6C

INTELLIGENT BIOSENSING METER

BACKGROUND OF THE INVENTION

1. Field of the Invention

The present invention relates in general to a biosensing meter. More particularly, the present invention relates to an intelligent biosensing meter that can store parameters therein, receive a code card with at least one parameter for transmitting the parameter into the intelligent biosensing meter or download at least one new parameter from Internet.

2. Description of the Related Art

The biosensing meter applied for detecting the substance contained in the blood to be analyzed, such as glucose or cholesterol normally employs a disposable sample strip to complete the inspection. The sample strip has a reaction well to allow blood dripped thereon. Via the combination of microprocessor/ROM, the whole operation is controlled. Further by executing various procedures, the analysis results for measurement are obtained. However, the advancement of technique continuously alters the operation procedure of measurement. To the bio-inspection field, the measurement factor is changed according to the manufacture of sample strip. However, if the hardware in the biosensing meter cannot be upgraded consequently, the purchased sensing meter is then inapplicable for the new batch of sample strips. As a result, the sensing meter has to be renewed. Such method is very impractical.

In order to account for lot-to-lot variation in the sample strips, it is commonplace for sample strip lots to be calibrated during their manufacture. Another conventional biosensing meter improves the above drawbacks by adding a slot on the biosensing meter. According to the position for plugging the sample strip, an additional code card is designed and inserted therein. While performing measurement, the code card has to be inserted in the biosensing meter all the time for the same batch of sample strips. According to the operation procedure and parameter provided by the code card, a correct measurement result is obtained.

However, some parameters, such as the intensity of a signal, an offset value, a measurement time, a temperature compensate parameter and so on, within the code card mated with each batch of the sample strip are variable when each batch of the sample strip is manufactured. Further, manufacturing the code card is expensive and waste time to control the manufacturing and administrative process. Therefore, some manufacturers make a conventional biosensing meter that stores a plurality of parameters in the biosensing meter such that the code card may not be manufactured. However, if a new batch of sample strip needs different parameter from that stored in the biosensing meter, the biosensing meter can not be used for measuring the new batch of sample strip.

SUMMARY OF THE INVENTION

In one aspect of the present invention, an intelligent biosensing meter in accordance with the present invention not only stores parameters therein but also can receive code card to store at least one new parameter or download at least one new parameter from Internet.

Accordingly, the intelligent biosensing meter of the present invention comprises a parameter storing unit, at least one button, at least one slot, a memory unit and a microprocessor. The parameter storing unit comprises a plurality of parameters that the sample strip detection needed. The slot is utilized for receiving a code card that stores at least one parameter therein that is not included in the parameter storing unit or a sample strip comprising a reaction well and a plurality of electrodes thereon in contact with the reaction well. The button is utilized for choosing different parameters. The memory unit is utilized for storing results or parameters stored in the code card or downloaded from Internet. The microprocessor is utilized for reading the parameters from the parameter storing unit or the memory unit for controlling operational procedures to measure an analyte in an analyte-containing fluid drawn into the reaction well of the sample strip and determining a measurement value of the analyte. Therefore, it will decrease cost for manufacturing code card if a parameter that a new batch of sample strip test needed is originally stored within the intelligent biosensing meter or downloaded from the Internet.

In another aspect of the present invention, an intelligent biosensing meter in accordance with the present invention can receive a code card, a sample strip or a check card by a single slot. The intelligent biosensing meter can recognize different cards or strips by different circuit design.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
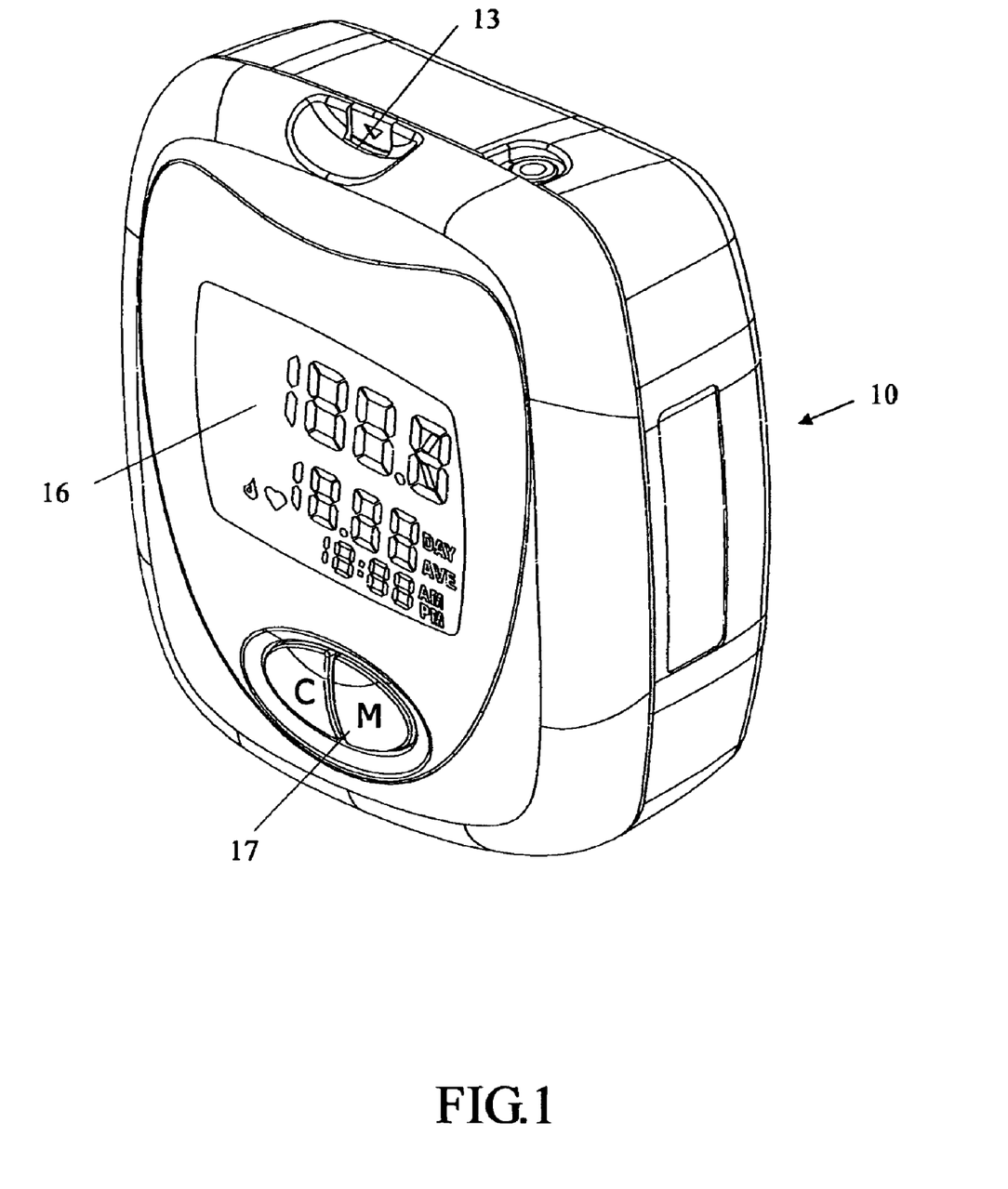
FIG. 1 is a perspective view of an intelligent biosensing meter in accordance with the present invention.
Figure 2:
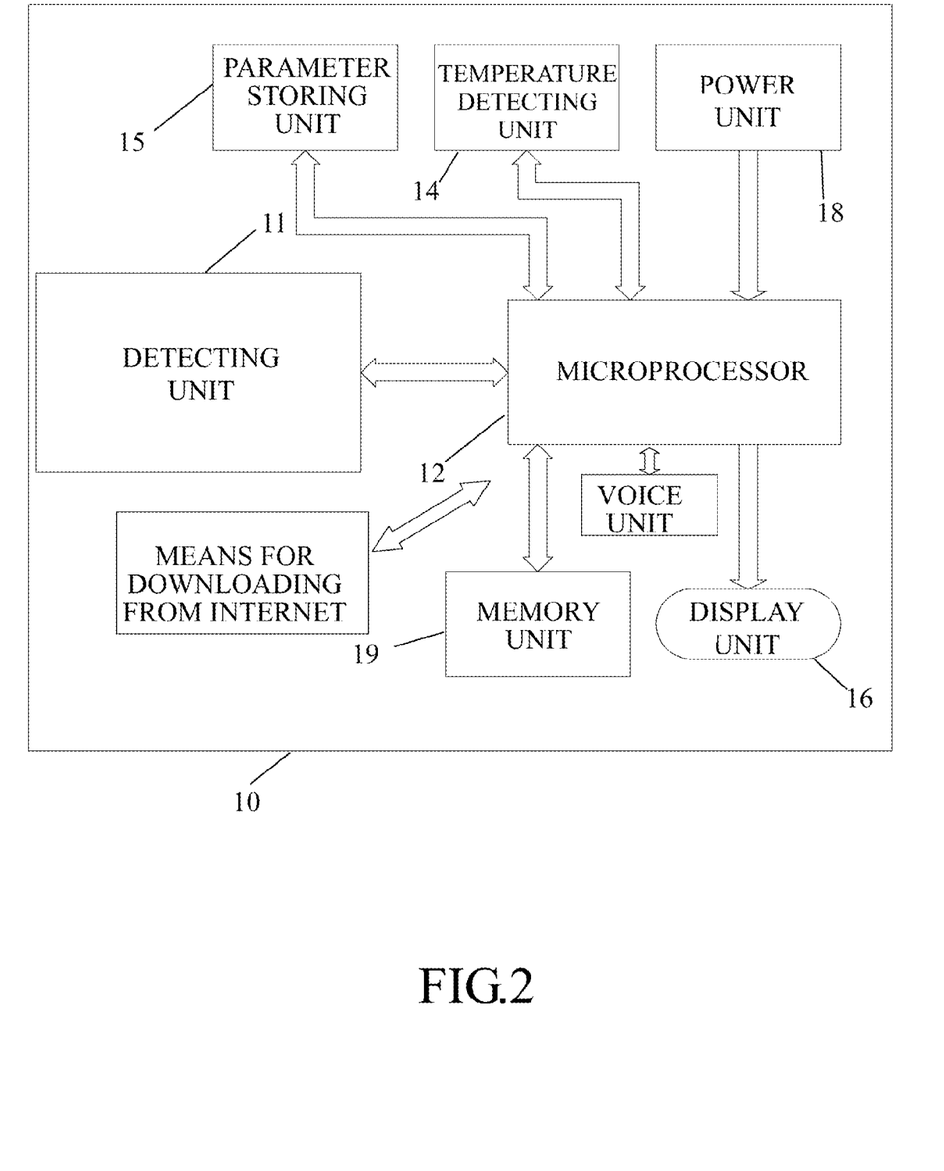
FIG. 2 is a block diagram of the intelligent biosensing meter in FIG. 1.

With reference to FIGS. 1 and 2, a biosensing meter (10) in accordance with the present invention comprises an operational detecting unit (11), a microprocessor (12), at least one slot (13), an operational temperature detecting unit (14), a parameter storing unit (15), an operational display unit (16), at least one button (17), an operational power unit (18) and a memory unit (19).

The power unit (18) can be utilized for supplying the biosensing meter (10) power. The slot (13) can receive a code card, a check card or a sample strip and preferably electrical connected with them. Preferably, the detecting unit (11) locates corresponding to the slot (13) and used for electrically connecting with the code card, check card or sample strip. The code card can store at least one parameter that is utilized for increasing test accuracy of a batch of sample strip. The check card employs to determine the operability of the biosensing meter (10). In a preferred embodiment of the present invention, the biosensing meter (10) comprises one slot (13) for receiving the code card, check card or sample strip.

When the sample strip plugged into the slot (13), the detecting unit (11) detects the electrochemical variation after the sample strip reacted with an analyte-containing fluid. In an embodiment of the present invention, the detecting unit (11) can recognize which kind of card inserted into the slot (13) and transmit the result to the microprocessor (12). If the code card inserted into the slot (13), the parameter stored within the code card transmits to and stores into the memory unit (19). In a preferred embodiment of the present invention, which kind of card inserted into the slot (13) is controlled by pressing the button (17) to choose different modes. Thus, pressing the button (17) to choose a code card mode while the code card is inserted into the slot (13) and recognized by the biosensing meter (10) or pressing the button (17) to choose a check card mode or sample strip mode while the suitable card is inserted into the slot (13) to be recognized. On the other hand, the card inserted into the slot (13) is recognized by operative modes or procedure modes.

The parameter storing unit (15) contains multiple parameters which can be chosen for testing suitable batch of sample strips. Preferably, the parameter storing unit (15) stores at least fifty series of parameters. More preferably, the parameter storing unit (15) stores one to fifty series of parameters. When the sample strip is manufactured, the sample strip is testing for providing one series of parameter which includes parameters converted between measurement values and real values, test time, temperature compensate parameter, measurement temperature threshold, alternative procedures or test parameter that different measurement substance needed. Once the sample strip is manufactured stably, the range of the parameter obtained from test result is not changed very much so storing some usually used parameter in the parameter storing unit (15) is enough for using. If the parameters obtained from tests fall into the range of the parameters stored in the parameter storing unit (15), users can operate the button (17) to choose the right parameter and then the test can proceed. Preferably, the parameter storing unit (15) is a read-only-memory (ROM) or electrically erasable programmable read-only memory (EEPROM).

In a preferred embodiment of the present invention, the parameter storing unit (15) contains fifty series of parameters and each series of parameter named No. 1 to No. 50. If parameters needed by the test fall into the range of the stored parameter in the parameter storing unit (15), the users just choose that number of parameter and then the biosensing meter (10) can be used to test that batch of sample strip. Furthermore, another method for choosing right parameter in the parameter storing unit (15) is provided by inserting different cards which respectively contains at least one resister circuit into the slot (13). For example, a variety of cards that have different resister values can be set respectively relation to a unique number of parameter, like a 10 k resister value related to No. 1 parameter, a 20 k resister value related to No. 2 parameter, a 30 k resister value related to No. 3 parameter and etc; therefore, inserting the related card into the slot (13) will let the biosensing meter (10) recognize it and then the biosensing meter (10) is entering the right mode for testing a mating batch of sample strip.

In another preferred embodiment of the present invention, the parameters stored in the parameter storing unit (15) are converting parameters between a measurement value and a real value of different substance test. For example, first to tenth series of parameters are converting parameters for testing blood glucose, eleventh to twentieth series of parameters are converting parameters for testing uric acid and twenty first to thirtieth series of parameters are converting parameters for testing pH. Therefore, the biosensing meter (10) can be used to choose for testing blood glucose, uric acid or pH. Furthermore, the parameters stored in the parameter are converting parameters for testing cholesterol so the biosensing meter (10) can be used for testing cholesterol.

The display unit (16) is used for displaying results, procedures, date, time and so on. The temperature detecting unit (17) is used for detecting temperature and obtaining temperature compensate parameter when the biosensing meter (10) needs to count the result if the temperature will influence the result The memory unit (19) is utilized for storing results or parameters when the parameters are not including in the range of the parameters stored in the parameter storing unit (15). The parameters not stored in the parameter storing unit (15) are stored in a code card that inserts into the slot (13) and then the parameters are stored in the memory unit (19) so that the biosensing meter can be used to test new substance or different batch of sample strip. Preferably, the memory unit (19) is an electrically erasable programmable read-only memory (EEPROM).

Furthermore, the biosensing meter (10) can download a new parameter from Internet and then store the parameter in the memory unit (19) for preventing manufacturing the code card to decrease cost. The biosensing meter (10) can receive the new parameter by a transmission line or by wireless. When the sample strip is manufactured and tests for defining a parameter value, for example, if the parameter is not included in the memory unit (19), the manufacturer can put the parameter in the internet and make an announcement for users and they can download the new parameter from the internet. Thus, the manufacturing cost is decreasing. In another aspect, the parameter storing unit (15) and the memory unit (19) are manufactured as one memory. In another preferred embodiment of the present invention, the biosensing meter further comprises a voicing unit and/or a communication unit The voicing unit can be used for sounding next steps, results, time and so on. The communication unit can be used for communicating date or information to other electronic device or other device.

Figure 3:
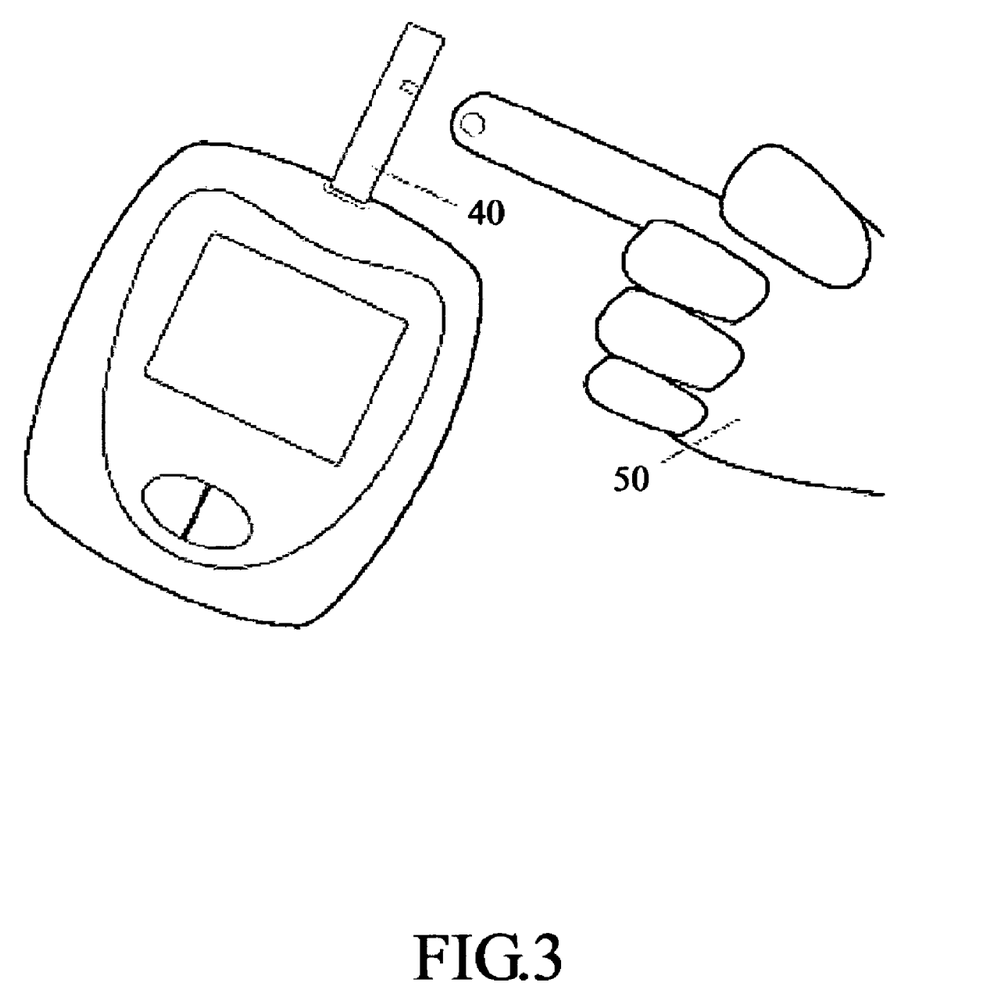
FIG. 3 is an operative view of the intelligent biosensing meter in FIG. 1.

With further reference to FIG. 3, the biosensing meter according to the present invention is used to measure an analyte, e.g. blood glucose. When an analyte-containing fluid, for example, a drop of blood from user's finger (50), has been received in a reaction well of the sample strip (40), an output signal corresponding to a sensing current is generated. With responding to the operation procedure and parameters in the memory, the microprocessor (12) determines a plurality of voltages with a predetermined lasting time. The voltages and the lasting time are obtained from the data stored in the code card (20) or the parameter storing unit (15). The microprocessor (12) controls to display an analysis result measured from the analyte-containing fluid.

Figure 4A:
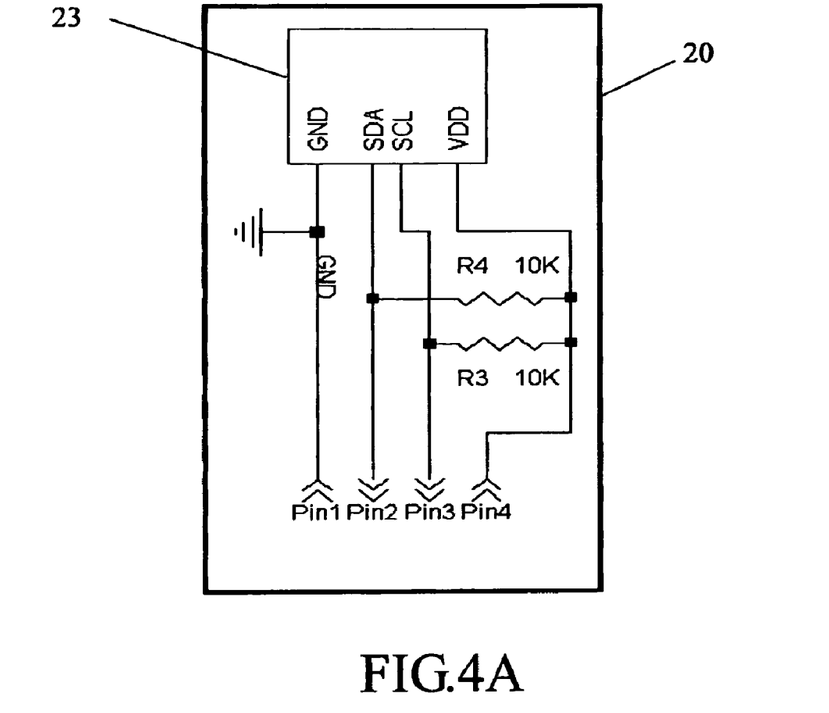
FIG. 4A is a circuit of a code card for inserting into the intelligent biosensing meter in FIG. 1.
Figure 4B:
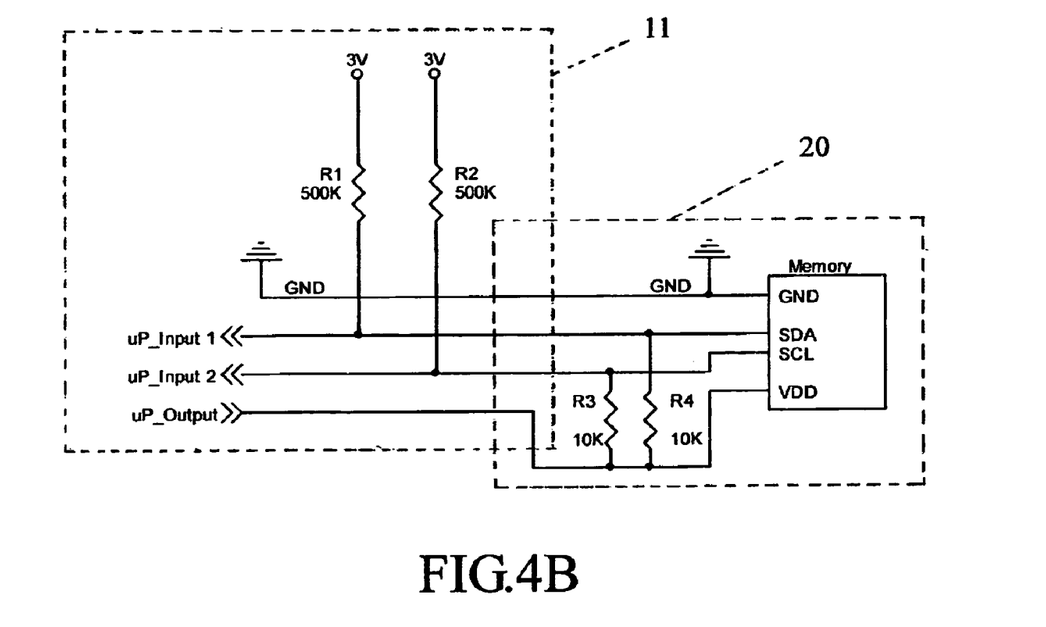
FIG. 4B is a circuit of the code card connected with a detecting unit of the intelligent biosensing meter in FIG. 1.
Figure 5A:
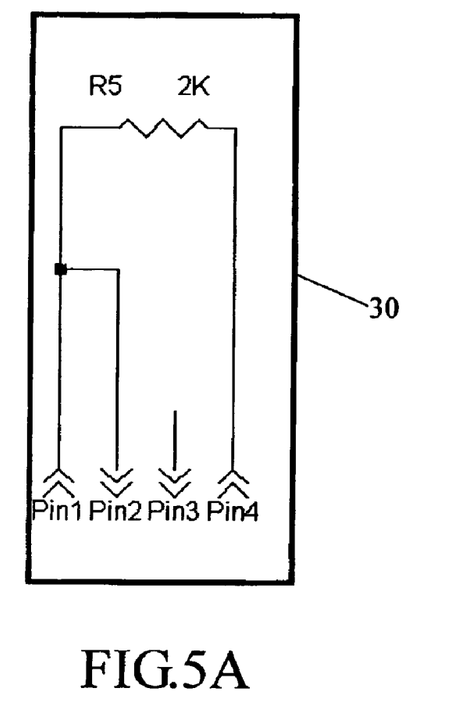
FIG. 5A is a first embodiment of a check card for inserting into the intelligent biosensing meter in FIG. 1.
Figure 5B:
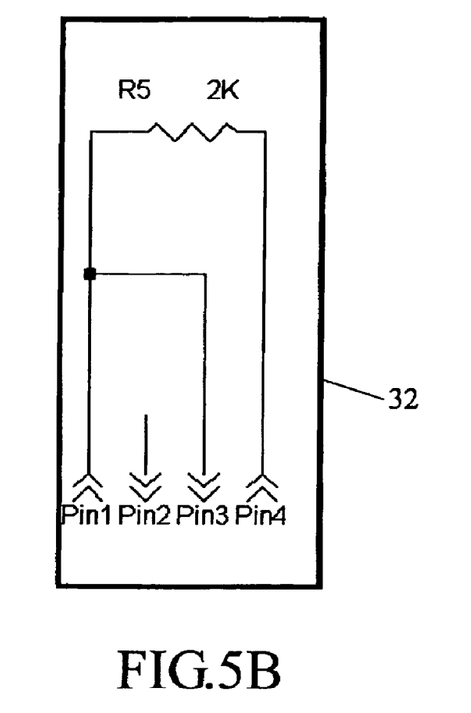
FIG. 5B is a second embodiment of a check card for inserting into the intelligent biosensing meter in FIG. 1.
Figure 5C:
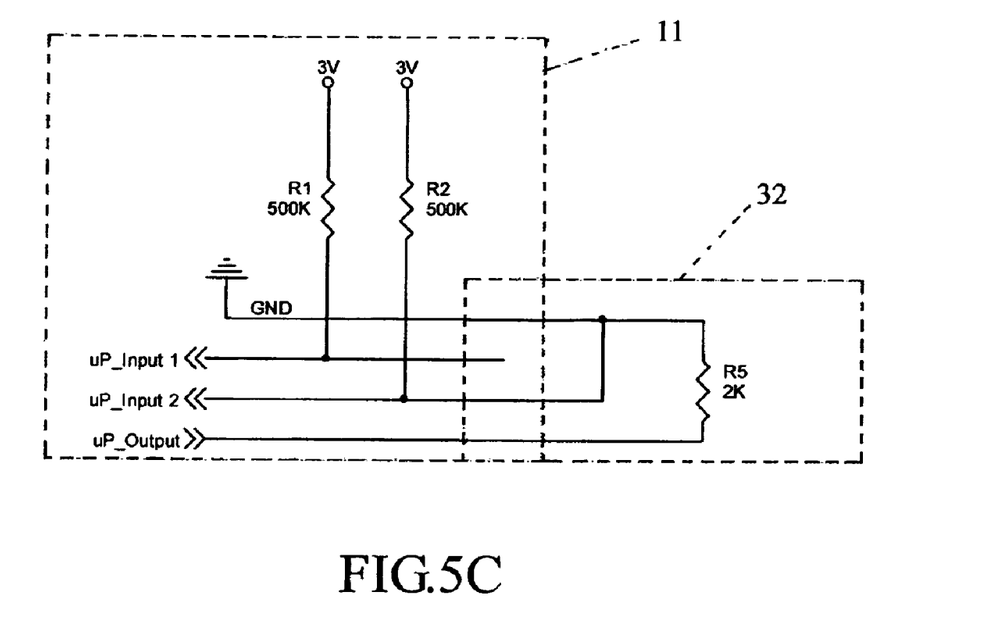
FIG. 5C is a circuit of the check card in FIG. 5B connected with the detecting unit of the intelligent biosensing meter in FIG. 1.
Figure 6A:
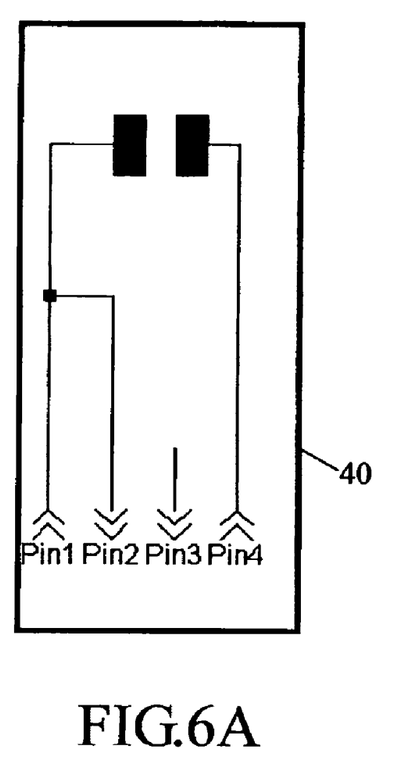
FIG. 6A is a first embodiment of a sample strip for inserting into the intelligent biosensing meter in FIG. 1.
Figure 6B:
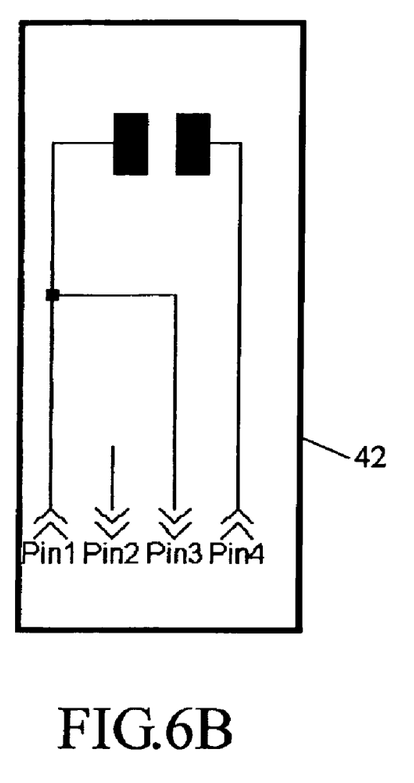
FIG. 6B is a second embodiment of the sample strip for inserting into the intelligent biosensing meter in FIG. 1.
Figure 6C:
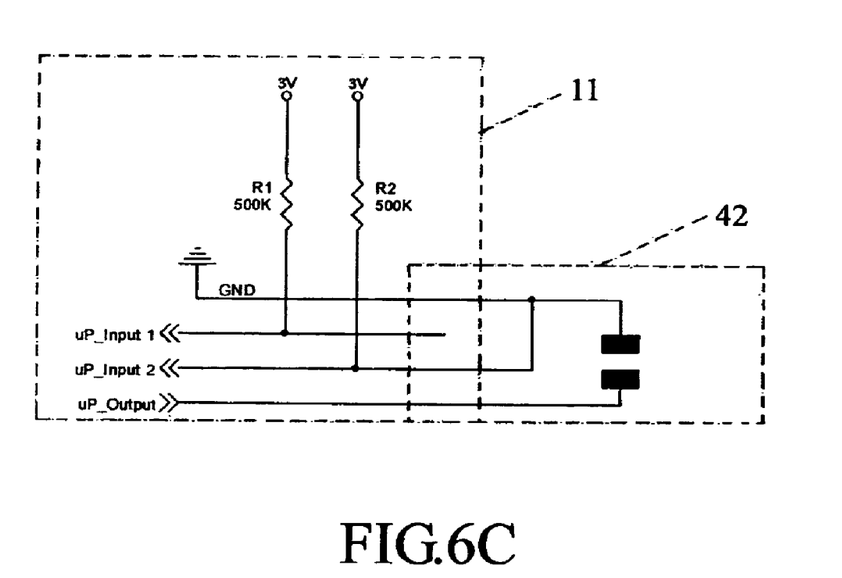
FIG. 6C is a circuit of the sample strip in FIG. 6B connected with the detecting unit of the intelligent biosensing meter in FIG. 1.

With further reference to FIGS. 4 to 6, the detecting unit (11) comprises electrical contacts for electrical connection with the code card (20), check card (30, 32) or sample strip (40, 42). Preferably, the detecting unit (11) comprises at least two electrical contacts mated with different kinds of variety strips or cards. As shown in Figures, the detecting unit (11) comprises four electrical contacts, named a first electrical contact, a second electrical contact, a third electrical contact and a fourth electrical contact, and two electrical contacts thereof each is connected with a voltage supply and a resistance. In the drawings, the third electrical contact and the fourth electrical contact each connects with a voltage supply and a resistance.

With further reference to FIGS. 4A and 4B, in a preferred embodiment of the present invention, the code card (20) comprises an electrically erasable programmable read-only memory (EEPROM) (23) for storing different parameters, and therefore, the biosensing meter (30) can test different batch of sample strip. In the figures, the code card (20) has four electrodes, named a first electrode, a second electrode, a third electrode and a fourth electrode, and two resistances. The two resistances are contacted respectively between the second and fourth electrodes and the third and fourth electrodes. When the code card (20) inserts into the slot (13), the electrodes on the code card (20) are electrically connected with the electrical contacts of the detecting unit (11). The voltage supply provides voltage to pass through the resistances of the detecting unit (11) and the code card (20) so that the voltage value that the microprocessor (12) detected is about zero. Therefore, the biosensing meter (10) can recognize which one inserts into the slot (13) is code card (20) by detecting the voltage value. Through transmitting the parameter stored in EEPROM (23) of the code card (20) to the memory unit (19) of the biosensing meter (10), the biosensing meter (10) can proceed a test for a matched batch of sample strip (40, 42).

With further reference to FIGS. 5A to 5C, the check card (30, 32) has four electrodes, named a first electrode, a second electrode, a third electrode and a fourth electrode, and a resistance connected with outer electrodes thereof. A first type of check card (30) has a short circuit connected between the first and the second electrodes (see FIG. 5A) and a second type of check card (32) has a short circuit connected between the first and the third electrodes (see FIG. 5B). The second type of check card (32), as an example, inserts into the slot (13) and connects with the detecting unit (11). The voltage supply provides a voltage passed through the resistances of the detecting unit (11) and the check card (32) so that the voltage value that the microprocessor (12) detected is about zero. Another voltage only passes through the resistance of the detecting unit (11) so that the voltage value that the microprocessor (12) detected is almost original voltage value. Furthermore, the check card (32) has a fixed resistance value so the microprocessor (12) can detect a stable current value that is greater than zero. Therefore, the microprocessor (12) can recognize the check card (32) by detecting the current and the voltage values.

With further reference to FIGS. 6A to 6C, the sample strip (40,42) comprises a reaction well and a plurality of electrodes thereon, there are four electrodes as an example in the drawings, named a first electrode, a second electrode, a third electrode and a fourth electrode. There is a short circuit formed between any two electrodes thereof and a first type of the sample strip (40) has a short circuit formed between the first and second electrodes (see FIG. 6A) and a second type of the sample strip (42) has a short circuit formed between the first and third electrodes (see FIG. 6B). A reactant is contained in the reaction well, while the electrodes are in contact with the reaction well. Taking the second type as an example, when the sample strip (42) inserts into the slot (13), a voltage provided by the voltage supply of the detecting unit (11) passes through the resistance of the detecting unit (11) so that the voltage value that the microprocessor (12) detected is almost the original voltage value. Another voltage supply of the detecting unit (11) provides another voltage to pass through the short circuit so that the voltage value that the microprocessor (12) detected is about zero. Furthermore, since the resistance value is a maximum, the current value that the microprocessor (12) detected is about zero, and therefore, the microprocessor (12) can recognize the sample strip (42) by detecting the voltage and the current values.

Therefore, the biosensing meter in accordance with the present invention can insert different kinds of card or strip into one slot and recognize by circuit design to control different functions. In a preferred embodiment of the present invention, since the check card, code card and the sample strip have different circuit design, the biosensing meter can recognize them by detecting voltage and current values. This will decrease cost and operating easily. Furthermore, the distributions of the electrodes which utilized for contact with the detecting unit on cards or strips are the same so the detecting unit unneeded to design again the structure of the detecting unit when there is a new card or strip designed.

Besides, the biosensing meter in accordance with the present invention not only stores parameters therein but also can receive code card to receive new parameter or download new parameter from an internet Manufacturers can save budget for manufacturing code card if parameters stored in the biosensing meter are suitable for testing a new batch of sample strip or download from the internet. Otherwise, if a new batch of sample strip needs a new series parameter, the biosensing meter can receive a code card that stored the new series parameter for upgrading to test the new batch of sample strip so the biosensing meter will not limit in the stored parameters.

Other embodiments of the invention will appear to those skilled in the art from consideration of the specification and practice of the invention disclosed herein. It is intended that the specification and examples to be considered as exemplary only, with a true scope and spirit of the invention being indicated by the following claims.

What is claimed is:

1. An intelligent biosensing meter comprising:
a parameter storing unit comprising a plurality of parameters that a sample strip detection needed;
   at least one slot for receiving a sample strip comprising a reaction well and a plurality of electrodes thereon in contact with the reaction well or a code card stored at least one parameter therein that is not included in the parameter storing unit;
   wherein the sample strip has a short circuit formed between two selected electrodes thereof for switching on the biosensing meter;
   at least one button for choosing different parameters stored in the parameter storing unit without the code card inserting into the slot;
   a memory unit for storing results or parameters stored in the code card; and
   a microprocessor for reading the parameters from the parameter storing unit or the memory unit for controlling operational procedures to measure an analyte in an analyte-containing fluid drawn into the reaction well of the sample strip and determining a measurement value of the analyte.

2. The intelligent biosensing meter as claimed in claim 1, wherein the memory unit is further utilized for storing at least one parameter downloaded from Internet and that parameter is not included in the parameter storing unit.

3. The intelligent biosensing meter as claimed in claim 2, wherein the memory unit downloads the parameter by wireless transmission.

4. The intelligent biosensing meter as claimed in claim 2, wherein the memory unit downloads the parameter by a transmission line.

5. The intelligent biosensing meter as claimed in claim 2, wherein the slot further receives a check card employed to determine the operability of the intelligent biosensing meter.

6. The intelligent biosensing meter as claimed in claim 5, further comprising a detecting unit located corresponding to the slot and electrically connection with the sample strip, code card or check card that received in the slot.

7. The intelligent biosensing meter as claimed in claim 6, wherein the detecting unit comprises at least two electrical contacts electrically connected with the sample strip, code card or check card.

8. The intelligent biosensing meter as claimed in claim 7, wherein the detecting unit recognizes the sample strip, code card or the check card by different circuit designs.

9. The intelligent biosensing meter as claimed in claim 8, wherein the check card comprises at least one resistance and at least two electrodes electrical connection with the detection unit.

10. The intelligent biosensing meter as claimed in claim 8, wherein the two electrical contacts of the detecting unit each connects with a voltage supply and a resistance.

11. The intelligent biosensing meter as claimed in claim 8, wherein the code card comprises two resistances connected with the electrodes respectively.

12. The intelligent biosensing meter as claimed in claim 1, further comprising a display unit, a temperature detecting unit, a power unit, a communication unit and/or at least one button.

13. The intelligent biosensing meter as claimed in claim 1, wherein the memory unit is electrically erasable programmable read-only memory.

14. The intelligent biosensing meter as claimed in claim 1, further comprising a plurality of slots for receiving a code card, a sample strip or a check card.

15. The intelligent biosensing meter as claimed in claim 1, wherein the parameter storing unit is read-only-memory or electrically erasable programmable read-only memory.

16. The intelligent biosensing meter as claimed in claim 1, wherein the parameter storing unit and the memory unit are formed integrally.

17. The intelligent biosensing meter as claimed in claim 1, which is utilized for testing blood glucose, uric acid, cholesterol or pH.

18. The intelligent biosensing meter as claimed in claim 1, wherein the slot further receives a card that contains at least one resister circuit for choosing different parameters.

19. The intelligent biosensing meter as claimed in claim 1, further comprising a voicing unit for voicing out.

* * * * *

US007514040C1

(12) EX PARTE REEXAMINATION CERTIFICATE (9535th)
United States Patent
Wu et al.

(10) Number: US 7,514,040 C1
(45) Certificate Issued: Feb. 27, 2013

(54) INTELLIGENT BIOSENSING METER

(75) Inventors: Shu-Mei Wu, Taipei (TW); Chia-Chi Wu, Kaohsiung (TW); Chun-Hui Pi, Yonghe (TW); Chao-Wang Chen, Taipei (TW)

(73) Assignee: Taidoc Technology Corporation, San-Chung, Taipei County (TW)

Reexamination Request:
No. 90/012,291, May 15, 2012

Reexamination Certificate for:
Patent No.: 7,514,040
Issued: Apr. 7, 2009
Appl. No.: 11/056,089
Filed: Feb. 14, 2005

(51) Int. Cl.
*G01N 15/06* (2006.01)
*G01N 33/00* (2006.01)
*G01N 33/48* (2006.01)
*G01N 1/00* (2006.01)
*G01N 27/28* (2006.01)
*G01N 31/00* (2006.01)
*G01N 33/50* (2006.01)
*G01N 33/487* (2006.01)
*C12M 1/00* (2006.01)
*C12N 9/00* (2006.01)
*C12N 11/00* (2006.01)
*C25B 9/00* (2006.01)
*C25B 11/00* (2006.01)
*C25B 13/00* (2006.01)

(52) U.S. Cl. .................................. 422/68.1; 204/403.02
(58) Field of Classification Search .................. None
See application file for complete search history.

(56) References Cited

To view the complete listing of prior art documents cited during the proceeding for Reexamination Control Number 90/012,291, please refer to the USPTO's public Patent Application Information Retrieval (PAIR) system under the Display References tab.

*Primary Examiner* — Robert Nasser (57) ABSTRACT

An intelligent biosensing meter has a parameter storing unit stored a plurality of parameters that sample strips detection needed and at least one slot for receiving a sample strip or a code card. The code card can store a plurality of parameters therein that are not stored in the parameter storing unit. Therefore, the intelligent biosensing meter not only stores parameters therein but also receives the code card to store new parameter or download new parameter from an internet. Manufacturers can save budget for manufacturing code cards if parameters stored in the biosensing meter are suitable for testing a new batch of sample strip or download from the internet. Furthermore, the intelligent biosensing meter can insert different kind of cards or strips into one slot and recognize them by circuit design to control different functions. The biosensing meter of the present invention will decrease manufacturing cost and be operated easily.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 5 and 6-11 are determined to be patentable as amended.

Claims 2-4 and 12-19, dependent on an amended claim, are determined to be patentable.

New claim 20 is added and determined to be patentable.

1. An intelligent biosensing meter comprising:
   a parameter storing unit comprising a plurality of parameters that a sample strip detection needed;
   at least one slot for receiving a sample strip comprising a reaction well and a plurality of electrodes thereon in contact with the reaction well [or a code card stored at least one parameter therein that is not included in the parameter storing unit]; wherein the sample strip has a short circuit formed between two selected electrodes thereof for switching on the biosensing meter;
   at least one button for choosing different parameters stored in the parameter storing unit [without the code card inserting into the slot];
   a memory unit for storing results [or parameters stored in the code card]; and
   a microprocessor for reading the parameters from the parameter storing unit or the memory unit for controlling operational procedures to measure an analyte in an analyte-containing fluid drawn into the reaction well of the sample strip and determining a measurement value of the analyte.

5. The intelligent biosensing meter as claimed in claim [2] *1*, wherein the slot further *selectively* receives a check card employed to determine the operability of the intelligent biosensing meter or *selectively receives a code card stored at least one parameter therein that is not included in the parameter storing unit.*

6. The intelligent biosensing meter as claimed in claim [5] *1*, further comprising a detecting unit located corresponding to the slot and electrically connection with the sample strip[, code card or check card] that received in the slot.

7. The intelligent biosensing meter as claimed in claim 6, wherein the detecting unit comprises at least two electrical contacts electrically connected with the sample strip[, code card or check card].

8. The intelligent biosensing meter as claimed in claim 7, wherein the detecting unit recognizes the sample strip[, code card or the check card] by different circuit designs.

9. The intelligent biosensing meter as claimed in claim [8] *5*, wherein the check card comprises at least one resistance and at least two electrodes electrical connection with the detection unit.

10. The intelligent biosensing meter as claimed in claim [8] *7*, wherein the two electrical contacts of the detecting unit each connects with a voltage supply and a resistance.

11. The intelligent biosensing meter as claimed in claim [8] *5*, wherein the code card comprises two resistances connected with the electrodes respectively.

20. *An intelligent biosensinq meter comprising:*
    *a parameter storing unit comprising a plurality of parameters that a sample strip detection needed;*
    *at least one slot for selectively receiving a sample strip comprising a reaction well and a plurality of electrodes thereon in contact with the reaction well and selectively receiving a code card stored at least one parameter therein that is not included in the parameter storing unit; wherein the sample strip has a short circuit formed between two selected electrodes thereof for switching on the biosensing meter;*
    *at least one button for choosing different parameters stored in the parameter storing unit without the code card inserting into the slot;*
    *a memory unit for storing results or parameters stored in the code card; and a microprocessor for reading the parameters from the parameter storing unit or the memory unit for controlling operational procedures to measure an analyte in an analyte-containing fluid drawn into the reaction well of the sample strip and determining a measurement value of the analyte.*

* * * * *